United States Patent [19]
Glennon

[11] Patent Number: 5,504,101
[45] Date of Patent: Apr. 2, 1996

[54] 5-HT-1D RECEPTOR LIGANDS

[75] Inventor: Richard A. Glennon, Richmond, Va.

[73] Assignee: Allelix Biopharmaceuticals, Inc., Ontario, Canada

[21] Appl. No.: 238,823

[22] Filed: May 6, 1994

[51] Int. Cl.[6] .................... C07D 209/04; A61K 31/40
[52] U.S. Cl. ............................................ 514/415; 548/504
[58] Field of Search ............................. 548/504; 514/415

[56] References Cited

U.S. PATENT DOCUMENTS 3,182,071  5/1965  Shavel .................................. 260/319

FOREIGN PATENT DOCUMENTS

| 1137489 | 12/1982 | Canada . |
| 287468 | 10/1988 | European Pat. Off. . |
| 327426 | 8/1989 | European Pat. Off. . |
| 191564 | 6/1990 | U.S.S.R. . |
| 859223 | 1/1961 | United Kingdom . |
| WO/9106537 | 5/1991 | WIPO . |
| WO/9300333 | 1/1993 | WIPO . |

OTHER PUBLICATIONS

CA 114:101728w Preparation . . . agonists. Fisher et al., p. 721, 1991.
CA 118:254747j Tryptamine . . . agonists. Kruse et al., p. 865, 1993.
Arutyunyan et al. "Relations between chemical structure and pharmacological activity of 5–alkoxytryptamines" Farmakoli Toksikool, 1964, 27(6):681 CA 62:15243c.
Buznikov et al. "Sensitivity of sea urchin early embryos to antagonists of acetylcholine and monoamines" Exp Cell Res. 1974, 86:317.
Buznikov et al. "The sensitivity of whole, half and quarter sea urchin embryos to cytotoxic neuropharmacological drugs" Comp Biochem Physiol, 1979, 64C:129.
Glennon et al. "Bufotenine ester" J Med Chem, 1979, 22(11):1414.
Glennon "5–HT$_{1D}$ receptors: a serotonin receptor population for the 1990s" DN&P, 1993, 6(6):390.
Glennon et al. "Central serotonin receptors as targets for drug research" J Med Chem, 1986, 30(1):1.
Glennon et al. "Serotonergic agents and CNS receptors" Advances in CNS Drug–Receptor Interactions 1:131, 1991.
Gomez–Jeria et al. "Quantum–chemical study of the relation between electronic structure and pA$_2$ in a series of 5–substituted tryptamines" Int J Quantum Chem, (1985) 28:421.
Gomez–Jeria et al. "Quantum chemical approach to the relationship between molecular structure and serotonin receptor binding affinity" J Pharmaceutical Sciences, 1984, 73(12):1725.
Gordeev et al. "Synthesis of 5–alkyltryptamines and 5–alkyl–alpha,–methyltryptamines" Mosk Khim–Tekhnol Inst. 1972, No. 70, 110 CA79(3):19057b.
Hibert et al. "Serotonin (5–HT) receptors", 1983 in *Comprehensive Medicinal Chemistry* vol. 3, ed. Sammes P., Pergamon Press, Oxford.
Hiemke et al. "Gas–liquid chromatographic properties of catecholamines, phenylethylamines and indolalkylamines as their propionyl derivatives" J Chromatography, 1978, 153:451.
Hino et al. "1–(–1–pyrrolin–2–yl)–β–carbolines. Synthesis of eudistomine H, I and P" Chem Pharm Bull, 1989, 37(10):2596.
Landau et al. "Sensitivity of sea urchin embryos to cytotoxic neuropharmacological drugs, the correlations between activity and lipophility of indole and benzole derivatives" Comp Biochem Physiol, 1981, 69C:359.
Morozovskaya et al. "O–acyl derivatives of serotonin" Pharm Chem J, 1968, 3:125.
Sleight et al. "Identification of 5–hydroxytryptamine1A receptor agents using a composite pharmacophore analysis and chemical database screening" Arch Pharm, 1991, 343:109.
von Strandtmann et al. "Acyltryptamines. II. Synthesis of acyltryptamines, indazoles, and azepinoindoles from the acylphenylhydrazones of 2,3–piperidinedione" J Med Chem, 1963, 6(6):719.
Suvorov et al. "Improved tryptamine synthesis" Zh Obshch Khim, 1964, 34:1595 CA 61:5598e.
Suvorov et al. "Amino acid and peptide derivatives of biogenetic amines IX. Synthesis of O,N–amino acid derivatives of serotonin and their mass spectrometirc and pharmacological study" Zh Obshch Khim, 1976, 46(5):1165 CA 86(7):44001f.
Vasin et al. "Role of the serotonin hydroxyl group in pharmacological and radioprotectant action of serotonin" Radiobiologiya, 1984, 23(3):411.

Primary Examiner—Joseph K. McKane
Attorney, Agent, or Firm—Nikaido, Marmelstein, Murray & Oram

[57] ABSTRACT

Described herein are tryptamine analogs that display high binding affinity and selectivity for the 5-HT1Dβ receptor, of the formula:

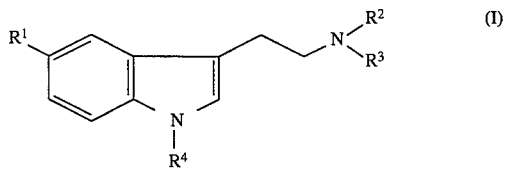

wherein

R[1] is a group selected from aryl-C$_{1-7}$alkyl; aryl-C$_{2-7}$alkoxy; aryl-C$_{2-7}$alkanoyl and aryl-C$_{1-7}$alkanoyloxy, wherein said alkyl, alkoxy, alkanoyl and alkanoyloxy groups are optionally substituted by a C$_{1-4}$ alkyl substituent and wherein said aryl group is optionally substituted by one or more substituent selected from hydroxyl, halogen, mercapto, linear or branched C$_{1-4}$alkyl, linear or branched C$_{1-4}$ alkoxy, linear or branched C$_{1-4}$alkylthio, thiol substituted C$_{1-4}$alkyl and nitro substituted C$_{1-4}$alkyl;

R[2] and R[3] are selected independently from H and C$_{1-4}$alkyl; and

R[4] is selected from H, C$_{1-4}$ alkyl, aryl and arylC$_{1-4}$alkyl. The compounds are useful as reagents for receptor identification and in receptor-based drug screening programs, and can also be used therapeutically to treat conditions for which administration of a 5-HT1D ligand is indicated, for example in the treatment of migraine.

20 Claims, No Drawings

5-HT-1D RECEPTOR LIGANDS

This invention relates to tryptamine analogs having 5-HT-1D receptor binding activity, and to their production and use.

BACKGROUND TO THE INVENTION

Through its interaction with receptors borne on neuronal and other cells, 5-hydroxytryptamine (5-HT; serotonin), exerts various physiological effects. Imbalances in this interaction are believed to be responsible for such conditions as anxiety, depression, hallucination, migraine, chemotherapy-induced nausea, and for disorders in sexual activity, cardiovascular activity and thermoregulation, among others. From an improved understanding of the 5-HT receptor population, it is apparent that these effects are mediated selectively through individual types and sub-types of 5-HT receptors. Migraine, for example, has been treated with ergotamine, dihydroergotamine and methysergide, all of which act at 5-HT-1D type receptors.

Given the physiological and clinical significance of the 5-HT-1D receptor, it would be desirable to provide compounds capable of binding with high affinity to this receptor, for medical use for example to treat indications such as migraine and others for which administration of a 5-HT-1D ligand is indicated, and also for diagnostic use for example to identify these receptors and to screen for drug candidates.

SUMMARY OF THE INVENTION

The present invention provides tryptamine analogs of formula (I) and salts, solvates or hydrates thereof:

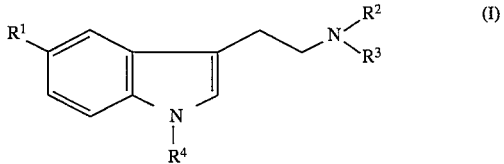

wherein
R$^1$ is a group selected from aryl-C$_{1-7}$alkyl; aryl-C$_{2-7}$alkoxy; aryl-C$_{2-7}$alkanoyl and aryl-C$_{3-7}$alkanoyloxy, wherein said alkyl, alkoxy, alkanoyl and alkanoyloxy groups are optionally substituted by a C$_{1-4}$ alkyl substituent and wherein said aryl group is optionally substituted by one or more substituents selected from hydroxyl, halogen, mercapto, linear or branched C$_{1-4}$alkyl, linear or branched C$_{1-4}$ alkoxy, linear or branched C$_{1-4}$alkylthio, thiol substituted C$_{1-4}$alkyl and nitro substituted C$_{1-4}$alkyl;

R$^2$ and R$^3$ are selected independently from H and C$_{1-4}$alkyl; and

R$^4$ is selected from H, C$_{1-4}$ alkyl, aryl and arylC$_{1-4}$alkyl.

Aspects of the present invention include compositions containing the present compounds either for use as reagents, for example in the identification of 5-HT-1D receptor ligands, or for pharmaceutical use to treat conditions where a 5-HT- 1D ligand is indicated.

DETAILED DESCRIPTION OF THE INVENTION AND PREFERRED EMBODIMENTS

The present invention provides tryptamine analogs that bind with relative high affinity to the 5-HT-1D. Compounds having this desirable property are tryptamine analogs in which the 5-position is substituted by a group, designated R$^1$, that is an alkyl, alkoxy, alkanoyl or alkanoyloxy, having a terminal aryl substituent. The aryl substituent is selected from aromatic carbocyclic rings such as benzene or the bicyclic ring naphthalene.

In specific embodiments of the invention, R$^1$ is phenyl-C$_{2-7}$alkoxy, preferably phenyl-C$_{2-5}$ alkoxy and most preferably 4-phenyl-butyloxy. In another embodiment of the invention, R$^1$ is phenyl-C$_{1-7}$alkyl optionally substituted on the aryl group by hydroxyl, halogen, linear or branched C$_{1-4}$alkyl and linear or branched C$_{1-4}$alkoxy, preferably phenyl-C$_{1-5}$alkyl optionally substituted at the para position with halogen or C$_{1-4}$alkoxy; and most preferably phenyl-C$_{1-2}$alkyl optionally substituted at the para position with methoxy. In other embodiment of the invention, R$^1$ is phenyl-C$_{2-7}$alkanoyl or phenyl-C$_{3-7}$alkanoyloxy.

R$^2$ and R$^3$ are selected independently from H, and C$_{1-4}$alkyl such as methyl and ethyl. In embodiments of the invention, at least one of R$^2$ and R$^3$ is H. R$^4$ is selected from H, C$_{1-4}$ alkyl, aryl and aryl-C$_{1-4}$alkyl. In specific embodiments of the invention, R$^2$, R$^3$ and R$^4$ are H. Particular compounds of formula (I) include:

3-(2-aminoethyl)-5-(2-phenylethyloxy)indole;
3-(2-aminoethyl)-5-(4-phenylbutyloxy)indole;
3-(2-aminoethyl)-5-(5-phenylpentyloxy)indole;
3-(2-aminoethyl)-5-(6-phenylhexyloxy)indole;
3-(2-aminoethyl)-5-benzylindole;
3-(2-aminoethyl)-5-(2-phenylethyl)indole;
3-(2-aminoethyl)-5-(2-(p-methoxyphenyl)ethyl)indole;

Acid addition salts of the compound of formula (I) include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of formula (I) for reagent use, or for subsequent conversion to a pharmaceutically acceptable acid addition salt. Also included within the scope of the invention are solvates and hydrates of the invention. The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

It will be appreciated that certain compounds of formula (I) for example where R$^1$ is substituted aryl-C$_{1-7}$alkyl, aryl-C$_{2-7}$alkoxy, aryl-C$_{3-7}$alkanoyloxy or aryl-C$_{2-7}$alkanoyl, may contain an asymmetric centre. Such compounds will exist as two (or more) optical isomers (enantiomers). Both the pure enantiomers and the racemic mixtures (50% of each enantiomer), as well as unequal mixtures of the two, are included within the scope of the present invention. Further, all diastereomeric forms possible (pure enantiomers and mixtures thereof) are within the scope of the invention.

The compounds of the present invention can be prepared by processes generally established in the art of organic synthesis. In the case where R$^1$ is aryl-C$_{1-7}$alkyl and R$^2$, R$^3$ and R$^4$ are hydrogen the following general procedure may be used. Synthesis originates from the position 5 substituent and proceeds to the formation of the indole ring by cyclization followed by activation at the 3 position and subsequent addition of the aminoethyl group. Synthesis begins by obtaining, from commercial sources or by synthesis, aniline substituted at the; para position with the desired aryl-alkyl group or aryl substituted aryl-alkyl group. For example, when $R^1$ is benzyl, commercially available 4-aminobenzophenone is reacted with HCl in the presence of a palladium catalyst to give the appropriate parabenzylaniline. When $R^1$ is 2-phenylethyl the appropriate p-(2-phenylethyl)aniline is obtained from p-nitrostilbene upon reaction of commercially available reagents p-nitrobenzoic acid and benzaldehyde. It will be appreciated that various substitutions may be introduced on the aryl group by incorporation of the substituent at this step of the synthesis provided the substituent is stable under subsequent reaction conditions. Suitable aryl substituents include hydroxyl, halogen, mercapto, linear or branched alkyl or alkoxy chains of 4 or fewer carbon atoms, $C_{1-4}$alkylthio, and nitro or thiol substituted $C_{1-4}$alkyl. Further, various aryl groups may be introduced including bicyclic aryl groups such as naphthyl. It will also be appreciated that the alkyl portion of the position 5 substituent may be branched provided that the main chain contains 7 or fewer carbon atoms and that the branches are of 4 or fewer carbon atoms.

A 5-substituted 2-alkoxycarbonylindole intermediate is obtained by reacting the parasubstituted aniline with first sodium nitrite and HCl and then 2-methylacetoacetate and KOH. The 2-alkoxycarbonyl group is removed with a suitable reagent such as KOH and the 3-position is activated with $POCl_3$ and dimethylformamide (DMF) to give a 5-substituted 3-formyl indole compound. This is converted to a 5-substituted 3-(2-nitro)ethenyl indole compound by reacting with nitromethane and ammonium acetate. Finally, reaction with lithium aluminum hydride ($LiAlH_4$) in tetrahydrofuran (THF) yields the desired 3-(2-aminoethyl)-5-(arylalkyl)indole compound of the invention. The following is a schematic representation of the synthesis of 5-(arylalkyl) compounds of the invention:

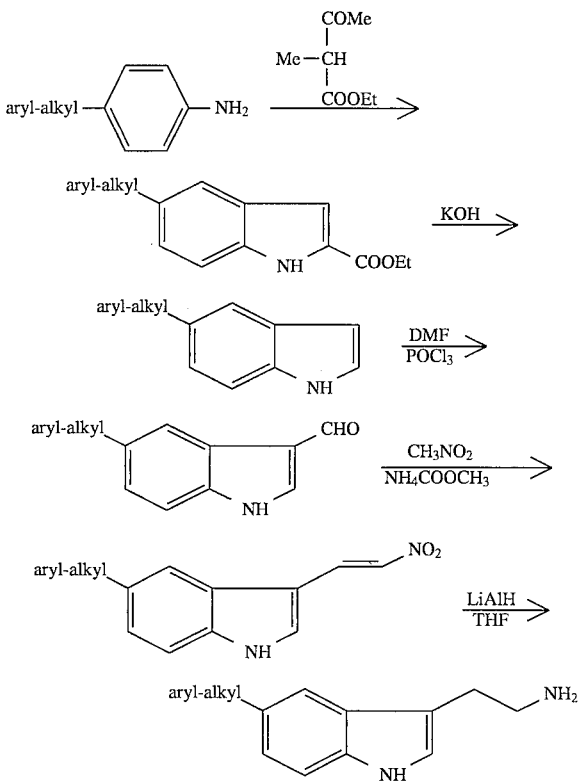

In the case where $R^1$ is aryl-$C_{1-7}$alkoxy and $R^2$, $R^3$ and $R^4$ are hydrogen the following general procedure may be used. Synthesis starts with commercially available 5-hydroxyindole which undergoes a substitution reaction with the desired aryl-alkylhalide with $K_2CO_3$ to give a 5-(arylalkoxy)-substituted indole. The aryl-alkylhalide may be synthesized or commercially obtained. It will be appreciated that various substitutions may be introduced on the aryl group by incorporation of the substituent at this step of the synthesis provided the substituent is stable under subsequent reaction conditions and that the alkoxy portion may be branched. Further, various aryl groups may be introduced including bicyclic aryl groups such as naphthyl. The 5-arylalkoxyindole compound is then reacted with oxalyl chloride followed by ammonium hydroxide to give a 3-(2-amino)dioxoethyl-5-arylalkoxyindole compound which is converted to the desired 3-(2-amino)ethyl-5-arylalkoxyindole of the invention by reacting with lithium aluminum hydride and tetrahydrofuran. The following is a schematic representation of the synthesis of 5-(arylalkoxy) compounds of the invention:

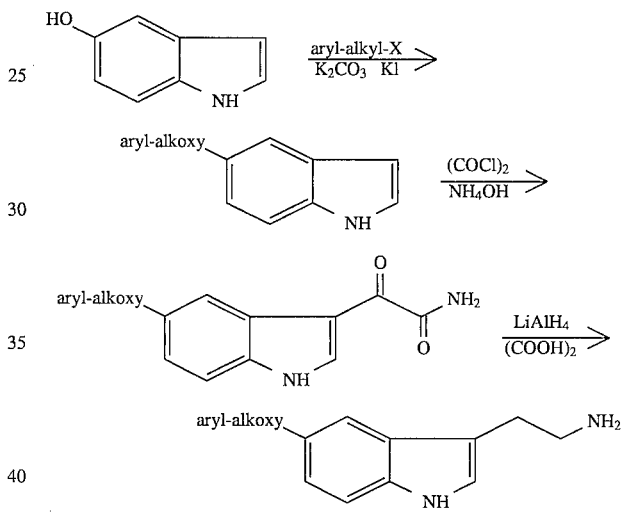

In the case where $R^1$ is aryl-$C_{2-7}$alkanoyl and $R^2$, $R^3$ and $R^4$ are hydrogen, the following general procedure described in von Strandtmann et al, J. Med. Chem. (1963) 6:719 may be used. Commercially obtained or synthesized p-aryl-$C_{2-7}$alkanoyl substituted benzenediazonium salts is coupled with 3-carboxy-2-piperidone to give a hydrazone. Cyclization of the hydrazone forms a 6-arylalkanoyl-1,2,3,4-tetrahydro-1-oxo-β-carboline which is converted to the corresponding 3-(2-aminoethyl)-5-arylalkanoylcarboxytryptamine by base-catalyzed hydrolysis. Decarboxylation by refluxing with HCl yields the desired 3-(2-aminoethyl)-5-arylalkanoylindole. It will be appreciated that the benzenediazonium salt may be substituted with aryl-alkanoyl groups that are branched or have further substitution on the aryl group. Suitable substituents are those that are stable under coupling, cyclization, hydrolysis and decarboxylation reaction conditions. The following is a schematic representation of the synthesis of 5-arylalkanoyl compounds of the invention:

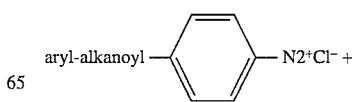

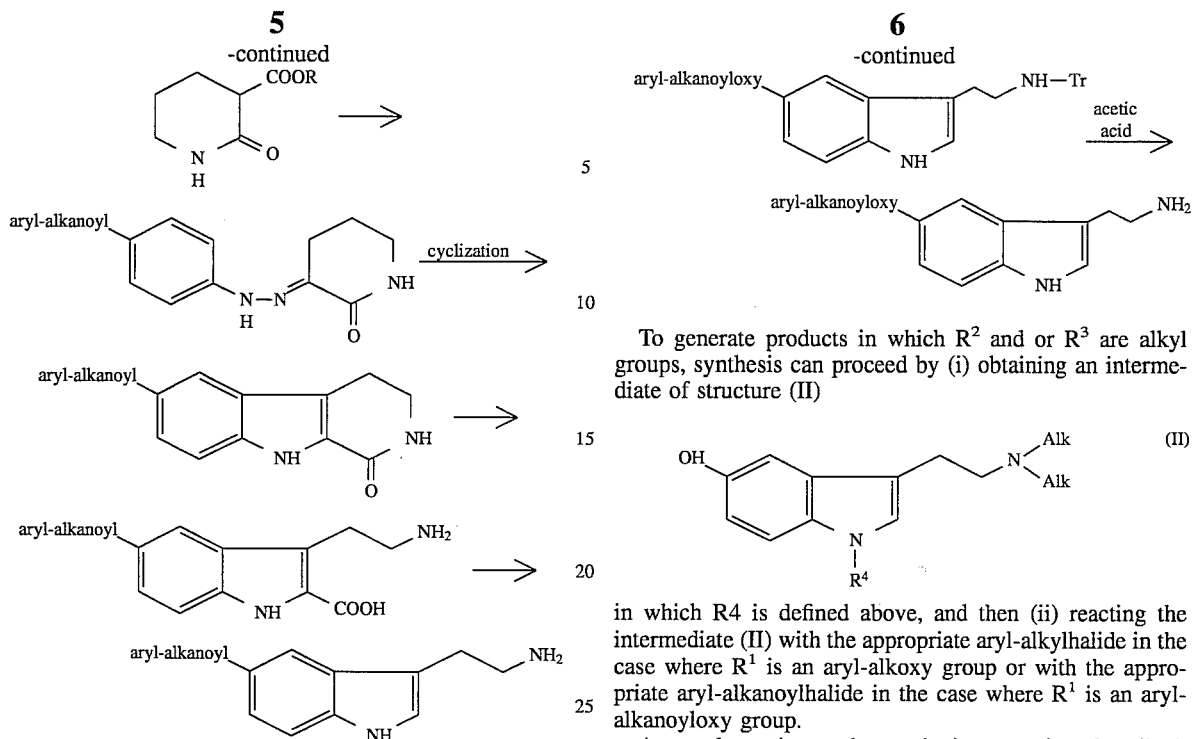

In the case where R¹ is aryl-$C_{3-7}$alkanoyloxy and R², R³ and R⁴ are hydrogen, the following general procedure described in Morozovskaya et al, Pharm. Chem. J. (1968) 3:125 may be used. Synthesis begins with an O-protected serotonin such as 3-(2-aminoethyl)-5-benzyloxyindole obtained as an intermediate in the synthesis of serotonin (Suvorov et al, Zh. Obshch. Khim. (1964) 34:1595) or by the procedures previously described for the synthesis of 5-arylalkoxy compounds of the invention. The 3-aminoethyl group is tritylated and the resulting amino-protected compound is then debenzylated by hydrogenation in an alcohol-:ethylacetate mixture in the presence of palladium catalyst to give 3-(2-N-tritylaminoethyl)-5-hydroxyindole (N-tritylserotonin). The 5-hydroxy group is converted to a $C_{3-7}$aryl-alkanoyloxy group by reacting with a corresponding $C_{3-7}$aryl-alkanoyl (optionally branched or substituted at the aryl group). Subsequently, the amino-protecting trityl group is removed with acetic acid to give the desired 3-(2-aminoethyl)-5-aryl-alkanoyloxyindole. The following is a schematic representation of the synthesis of 5-arylalkanoyloxy compounds of the invention:

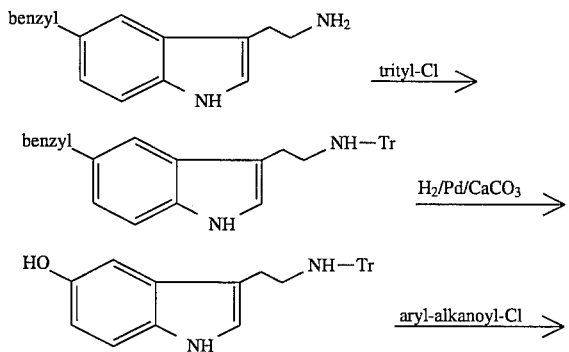

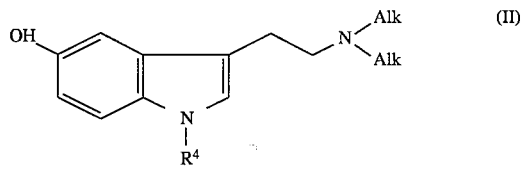

To generate products in which R² and or R³ are alkyl groups, synthesis can proceed by (i) obtaining an intermediate of structure (II)

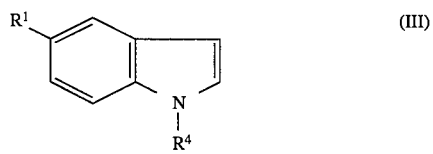

in which R4 is defined above, and then (ii) reacting the intermediate (II) with the appropriate aryl-alkylhalide in the case where R¹ is an aryl-alkoxy group or with the appropriate aryl-alkanoylhalide in the case where R¹ is an aryl-alkanoyloxy group.

As an alternative to the synthetic routes just described, and particularly for the production of compounds in which both R² and R³ are $C_{1-4}$alkyl, compounds of formula (I) can be prepared by the steps of obtaining an intermediate of structure (III)

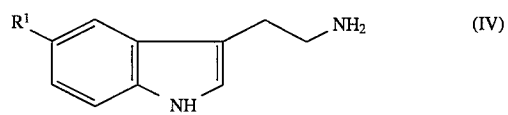

wherein R¹ is an aryl-alkyl, aryl-alkoxy, aryl-alkanoyl or aryl-alkanoyloxy and R⁴ is defined above, and then elaborating to the corresponding aminoethyl or substituted amino ethyl. This elaboration can be achieved using procedures established in the art, for instance, by reaction of intermediate (III) with oxalyl chloride and subsequent amidation by reaction with NHR²R³. Reduction of the resulting glyoxylic amide with a suitable reducing agent, such as lithium aluminum hydride, will yield the desired compound of formula (I).

To generate products in which R⁴ is an alkyl, aryl or arylalkyl group, synthesis can proceed by (i) obtaining a compound of structure (IV)

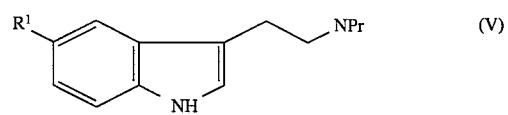

by methods previously described wherein R¹ is aryl-alkyl, aryl-alkoxy, aryl-alkanoyl or aryl-alkanoyloxy ii) protecting the aminoethyl nitrogen with a suitable protecting group, for example pthalimide to give a compound (V)

$$\text{(V)}$$

iii) reacting compound (V) with the desired alkyl, aryl or arylalkyl halide and finally iv) deprotecting the aminoethyl group with the appropriate deprotecting agent, such as hydrazine when the protecting group is a phthalimide.

In an embodiment of the invention, the compound is provided in labelled form, such as radiolabelled form e.g. labelled by incorporation within its structure $^3$H or $^{14}$C or by conjugation to $^{125}$I. In another aspect of the invention, the compounds in labelled form can be used to identify 5-HT-1D receptor ligands by techniques common in the art. This can be achieved by incubating the receptor in the presence of a ligand candidate and then incubating the resulting preparation with an equimolar amount of radiolabelled compound of the invention such as 5-(4-phenylbutyloxy)-3-(2-aminoethyl)indole. 5-HT-1D ligands are thus revealed as those that are not significantly displaced by the radiolabelled compound of the present invention. Alternatively, 5-HT-1D ligand candidates may be identified by first incubating a radiolabelled form of a compound of the invention then incubating the resulting preparation in the presence of the candidate ligand. A more potent 5-HT-1D ligand will, at equimolar concentration, displace the radiolabelled compound of the invention.

The serotonin-like binding affinity of the present compounds indicates their utility as pharmaceuticals that may be useful for the treatment of various conditions in which the use of a 5-HT-1D ligand is indicated, such as for the treatment of migraine, cluster headache and portal tension, a condition characterized by increased portal vein blood flow and typically associated with cirrhosis of the liver.

For use in medicine, the compounds of the present invention are administered in a standard pharmaceutical composition. The present invention therefore provides in a further aspect pharmaceutical compositions comprising a compound of structure (I) or a pharmaceutically acceptable salt, solvate or hydrate thereof and a pharmaceutically acceptable carrier. The compounds of the present invention may be administered by any convenient route; for example by oral, parenteral, buccal, sublingual, nasal, rectal or transdermal administration and the pharmaceutical compositions adapted accordingly.

The compounds and their pharmaceutically acceptable salts which are active when given orally can be formulated as liquids, for example syrups, suspensions or emulsions, tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene, glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsules; alternatively, a dispersion or suspension can be prepared using any suitable pharmaceutical carrier, for example aqueous gums, celluloses, silicates or oils and the dispersion or suspension filled into soft gelatin capsules.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration. Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 01. to 25 mg) of a compound of the formula (I) or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g., between 10 mg and 250 mg, or an intravenous, subcutaneous, or intramuscular dose of between 0.1 mg and 100 mg, preferably between 0.1 mg and 50 mg, e.g., between 1 mg and 25 mg, of the compound of formula (I) or a pharmaceutically acceptable salt, solvate or hydrate thereof calculated as the free base, the compound being administered 1 to 4 times per day. Suitably, the compounds will be administered for a period of continuous therapy, for example for a week or more.

EXAMPLE 1

3-(2-aminoethyl)-5-(2-phenylethyloxy)indole

A stirred mixture of 5-hydroxyindole (0.5 g, 3.8 mmol), anhydrous $K_2CO_3$ (1.58 g, 11.4 mmol), (2-bromoethyl) benzene (2.11 g, 11.4 mmol), and a catalytic amount of KI in 2-butanone (40 ml) was heated at reflux overnight under nitrogen. Once cooled to room temperature, the reaction mixture was filtered and the flitrate concentrated under reduced pressure to give an oil. The oil was taken up in $CH_2Cl_2$ (50 ml) and washed successively with 2N-NaOH (1×20 ml) and water (1×20 ml). The organic portion was dried ($MgSO_4$) and the solvent was removed under reduced pressure to give an oil. The oil was purified by column chromatography using a solvent system of $CH_2Cl_2$/Hexane (40:60) to give 0.42 g (47%) of 5-(2-phenylethyloxy)indole as an oil.

A solution of oxalyl chloride (0.39 g, 3.04 mmol) in anhydrous ether (10 ml) was added dropwise to a solution of the 5-(2-phenylethyloxy)indole (0.6 g, 2.53 mmol) in anhydrous ether (20 ml) at 0° C. The reaction mixture was stirred at room temperature for 1 h. The bright yellow precipitate formed was collected by filtration, washed with anhydrous Et$_2$O (2×20 ml), and immediately added to concentrated NH$_4$OH (20 ml) at 0° C. The basic solution was stirred at room temperature for 4 h and the solid was collected by filtration, washed with water (3×20 ml), air-dried, and recrystallized from acetone/hexane to afford 0.5 g (74%) of 3-(2-amino-1,2-dioxoethyl)-5-(2-phenylethyloxy)indole as a light yellow solid, mp 217°–218° C. (with decomposition).

A suspension of the 3-(2-amino-1,2-dioxoethyl)-5-(2-phenylethyloxy)indole (0.4 g, 1.3 mmol) and LiAlH$_4$ (0.32 g, 8.44 mmol) in dry THF (30 ml) was then heated at reflux for 3 days under nitrogen. After allowing the reaction mixture to cool to room temperature, the excess LiAlH$_4$ was decomposed by the addition of a saturated solution of sodium potassium tartrate (3 ml) at 0° C. The precipitated material was removed by filtration and the flitrate was dried (MgSO$_4$). The solvent was removed under reduced pressure to afford an oily product. The oil was purified by column chromatography using a solvent system of CH$_2$Cl$_2$/MeOH (90:10) to provide 0.14 g (38%) of 3-(2-aminoethyl)-5-(2-phenylethyloxy)indole hemioxalate as an oil. The oil was taken up in anhydrous Et$_2$O(5 ml) and added to a saturated ethereal solution of oxalic acid. The resultant oxalate salt was collected by filtration, washed with anhydrous Et$_2$O (2×10 ml), and recrystallized from MeOH/Et$_2$O to afford a white solid; mp 174°–176° C. Analytically calculated formula C$_{18}$H$_{20}$N$_2$O. 1/2 (COOH)$_2$. 1/4H$_2$O).

EXAMPLE 2

3-(2-aminoethyl)-5-(4-phenylbutyloxy)indole

A stirred mixture of 5-hydroxyindole (0.5 g, 3.8 mmol), anhydrous K$_2$CO$_3$ (1.58 g, 11.4 mmol), (4-bromobutyl)benzene (2.11 g, 11.4 mmol), and a catalytic amount of KI in 2-butanone (40 ml) was heated at reflux overnight under nitrogen. After allowing to cool to room temperature, the reaction mixture was filtered, the flitrate then concentrated under reduced pressure to give an oil. The oil was taken up in CH$_2$Cl$_2$ (50 ml) and washed successively with 2N-NaOH (1×20 ml) and water (1×20 ml). The organic portion was dried (MgSO$_4$) and the solvent was removed under reduced pressure to give an oil. The oil was purified by column chromatography using a solvent system of CH$_2$Cl$_2$/Hexane (40:60) to give 5-(4-phenylbutyloxy)indole as an oil.

A solution of oxalyl chloride (0.39 g, 3.04 mmol) in anhydrous ether (10 ml) was added dropwise to a solution of the 5-(4-phenylbutyloxy)indole (0.6 g, 2.53 mmol) in anhydrous ether (20 ml) at 0° C. The reaction mixture was stirred at room temperature for 1 h. The precipitate formed was collected by filtration, washed with anhydrous Et$_2$O (2×20 ml), and immediately added to concentrated NH$_4$OH (20 ml) at 0° C. The basic solution was stirred at room temperature for 4 h and the solid was collected by filtration, washed with water (3×20 ml), air-dried, and recrystallized from acetone/hexane to afford 3-(2-amino- 1,2-dioxoethyl)-5-(4-phenylbutyloxy)indole as a solid.

A suspension of the 3-(2-amino-1,2-dioxoethyl)-5-(4-phenylbutyloxy)indole (0.4 g, 1.3 mmol) and LiAlH$_4$ (0.32 g, 8.44 mmol) in dry THF (30 ml) was heated at reflux for 3 days under nitrogen. After allowing the reaction mixture to cool to room temperature, the excess LiAlH$_4$ was decomposed by the addition of a saturated solution of sodium potassium tartrate (3 ml) at 0° C. The precipitated material was removed by filtration and the flitrate was dried (MgSO$_4$). The solvent was removed under reduced pressure to afford an oily product. The oil was purified by column chromatography using a solvent system of CH$_2$Cl$_2$/MeOH (90:10) to provide 3-( 2-aminoethyl)-5-(4-phenylbutyloxy)indole (32.8% yield) as an oil. The oil was taken up in anhydrous Et$_2$O (5 ml) and added to a saturated ethereal solution of oxalic acid. The resultant oxalate salt was collected by filtration, washed with anhydrous Et$_2$O (2×10 ml), and recrystallized from MeOH/Et$_2$O to afford a tan solid; mp 130°–132° C. Analytically calculated formula C$_{20}$H$_{24}$N$_2$O. (COOH)$_2$.

EXAMPLE 3

3-(2-aminoethyl)-5-(5-phenylpentyloxy)indole

Synthesis of 3-(2-aminoethyl)-5-(5-phenylpentyloxy)indole was based on the protocols of example 1. A stirred mixture of 5-hydroxyindole (0.5 g, 3.8 mmol), anhydrous K$_2$CO$_3$, (2-bromopentyl)benzene, and a catalytic amount of KI in 2-butanone (40 ml) was heated at reflux overnight under nitrogen. After allowing to cool to room temperature, the reaction mixture was filtered, the flitrate was then concentrated under reduced pressure to give an oil. The oil was taken up in CH$_2$Cl$_2$ (50 ml) and washed successively with 2N-NaOH (1×20 ml) and water (1×20 ml). The organic portion was dried (MgSO$_4$) and the solvent was removed under reduced pressure to give an oil. The oil was purified by column chromatography using a solvent system of CH$_2$Cl$_2$/Hexane (40:60) to give 5-(5-phenylpentyloxy)indole as an oil.

A solution of oxalyl chloride in anhydrous ether (10 ml) was added dropwise to a solution of the 5-(5-phenylpentyloxy)indole in anhydrous ether (20 ml) at 0° C. The reaction mixture was stirred at room temperature for 1 h. The bright yellow precipitate formed was collected by filtration, washed with anhydrous Et$_2$O(2×20 ml), and immediately added to concentrated NH$_4$OH (20 ml) at 0° C. The basic solution was stirred at room temperature for 4 h and the solid was collected by filtration, washed with water (3×20 ml), air-dried, and recrystallized from acetone/hexane to give 3-(2-amino-1,2-dioxoethyl)-5-(5-phenylpentyloxy)indole.

A suspension of the 3-(2-amino-1,2-dioxoethyl)-5-(5-phenylpentyloxy)indole and LiAlH$_4$ in dry THF (30 ml) was heated at reflux for 3 days under nitrogen. After allowing the reaction mixture to cool to room temperature, the excess LiAlH$_4$ was decomposed by the addition of a saturated solution of sodium potassium tartrate (3 ml) at 0° C. The precipitated material was removed by filtration and the filtrate was dried (MgSO$_4$). The solvent was removed under reduced pressure to afford an oily product. The oil was purified by column chromatography using a solvent system of CH$_2$Cl$_2$/MeOH (90:10) to give the product as an oil. The oil was taken up in anhydrous Et$_2$O(5 ml) and added to a saturated ethereal solution of oxalic acid. The resultant 3-( 2-aminoethyl)-5-(5-phenylpentyloxy)indole hemioxalate salt was collected by filtration, washed with anhydrous Et$_2$O (2×10 ml), and recrystallized from MeOH/Et$_2$O to afford a white solid (23.9%); mp 170°–180° C. Analytically calculated formula C$_{21}$H$_{26}$N$_2$O. 1/2 (COOH)$_2$ . 1/4 H$_2$O):

EXAMPLE 4

3-(2-aminoethyl)-5-(6-phenylhexyloxy)indole

Synthesis of 3-(2-aminoethyl)-5-(6-phenylhexyloxy)indole was based on the protocols of example 1. A stirred mixture of 5-hydroxyindole (0.5 g, 3.8 mmol), anhydrous K$_2$CO$_3$, (2-bromohexyl)benzene, and a catalytic amount of KI in 2-butanone (40 ml) was heated at reflux overnight under nitrogen. After allowing to cool to room temperature, the reaction mixture was filtered, the filtrate concentrated under reduced pressure to give an oil. The oil was taken up in CH$_2$Cl$_2$ (50 ml) and washed successively with 2N-NaOH (1×20 ml) and water (1×20 ml). The organic portion was dried (MgSO$_4$) and the solvent was removed under reduced pressure to give an oil. The oil was purified by column chromatography using a solvent system of CH$_2$Cl$_2$/Hexane (40:60) to give 5-(6-phenylhexyloxy)indole as an oil.

A solution of oxalyl chloride in anhydrous ether (10 ml) was added dropwise to a solution of the 5-(6-phenylhexyloxy)indole in anhydrous ether (20 ml) at 0° C. The reaction mixture was stirred at room temperature for 1 h. The bright yellow precipitate formed was collected by filtration, washed with anhydrous Et$_2$O (2×20 ml), and immediately added to concentrated NH$_4$OH (20 ml) at 0 ° C. The basic solution was stirred at room temperature for 4 h and the solid was collected by filtration, washed with water (3×20 ml), air-dried, and recrystallized from acetone/hexane to give 3-(2-amino-1,2-dioxoethyl)-5-(6-phenylhexyloxy)indole.

A suspension of the 3-(2-amino-1,2-dioxoethyl)-5-(6-phenylhexyloxy)indole and LiAlH$_4$ in dry THF (30 ml) was heated at reflux for 3 days under nitrogen. After allowing the reaction mixture to cool to room temperature, the excess LiAlH$_4$ was decomposed by the addition of a saturated solution of sodium potassium tartrate (3 ml) at 0° C. The precipitated material was removed by filtration and the filtrate was dried (MgSO$_4$). The solvent was removed under reduced pressure to afford an oily product. The oil was purified by column chromatography using a solvent system of CH$_2$Cl$_2$/MeOH (90:10) to give the product as an oil. The oil was taken up in anhydrous Et$_2$O (5 ml) and added to a saturated ethereal solution of oxalic acid. The resultant 3-(2-aminoethyl)-5-(6-phenylhexyloxy)indole hemioxalate salt was collected by filtration, washed with anhydrous Et$_2$O (2×10 ml), and recrystallized from MeOH/Et$_2$O to afford a white solid (26%); mp 180°–183°C. Molecular formula C$_{44}$H$_{56}$N$_4$O$_2$. (COOH)$_2$. 1/4 H$_2$O):

EXAMPLE 5

3-(2-aminoethyl)-5-benzylindole

A solution of 4-aminobenzophenone hydrochloride (3 g, 13 mmol) in a mixture of acetic acid (90 ml) and perchloric acid 70% (7 ml) and 10% Pd/C (0.3 g) was hydrogenated at room temperature (44 psi) for 18 h. The catalyst was removed by filtration and the solvent was evaporated under reduced pressure. The crude product was dissolved in EtOH 50% (15 ml) and diluted with 50% NaOH to pH 12. H$_2$O (20 ml) was added and the mixture was extracted with CH$_2$Cl$_2$ (3×25 ml). The CH$_2$Cl$_2$ solution was washed with 20 ml of H$_2$O (dried MgSO$_4$) and evaporated in vacuo to give 2 g (85%) of the free base as an oil. The free base was dissolved in anhydrous Et$_2$O and treated with ethereal HCl. The precipitate was collected by filtration and recrystallized from absolute EtOH to afford the product p-benzylaniline hydrochloride mp 219°–221° C.

Solid NaNO$_2$ (0.35 g, 5 mmol) was added to a suspension of the pobenzylaniline (1.1 g, 5 mmol) and concentrated HCl (2 ml) in H$_2$O (3 ml) under an ice-water bath. The solution was kept at −5° C. with stirring while ethyl 2-methylacetoacetate (0.72 g, 5 mmol) in EtOH 95% (5 ml) was treated at −10° C. with a solution of 50% KOH (1.7 ml) followed at once by ice (10 g). The solution was then added immediately, stirred at room temperature for 20 min, and extracted with Et$_2$O (2×20 ml). The combined Et$_2$O portions were dried (MgSO$_4$) and the solvent was removed under reduced pressure to give a red oil which was taken up in anhydrous EtOH (10 ml), and dry hydrogen chloride gas was passed through the solution until ammonium chloride was precipitated. The mixture was heated at reflux for 20 min, and then stirred at room temperature for 2 h. The suspension was poured into ice water (100 ml) and extracted with Et$_2$O (2×30 ml). The combined Et$_2$O portions were dried (MgSO$_4$) and the solvent was removed under reduced pressure to give a solid which was recrystallized from EtOH 95% to provide 0.44 g (33%) of 5-benzyl-3-ethyloxycarbonylindole as a yellow solid, mp 119°–121° C.

To a solution of the 5-benzyl-3-ethyloxycarbonylindole (0.4 g, 1.5 mmol) in EtOH 95 % (10 ml) was added an excess of KOH (0.5 g) and the reaction mixture was heated at reflux for 2 h. The solution was acidified with 1N HCl (10 ml) and the precipitated material was collected by filtration. The solid was washed well with H$_2$O (2×10 ml) to give 0.34 g (95%) the acid as an ivory solid, mp 225°–228° C. The acid (0.3 g, 1.2 mmol) was immersed in an oil bath and then heated at about 235°–240° C. for 15 min to give a brown syrup. Distillation of the oil under high vacuum provided 0.07 g (28%) of 5-benzylindole as a tan oil.

Freshly distilled POCl$_3$ (0.122 ml) was added dropwise to cooled (ice bath) dry DMF (0.4 ml). The mixture was stirred 0.5 h at 0° C., then a solution of 5-benzylindole (0.24 g, 1.2 mmol) in DMF (0.14 ml) was added dropwise, during which time the temperature was maintained below 10° C. Once the solution was well mixed, the temperature was brought to 35° C. The syrup was stirred efficiently at this temperature for 1 h. At the end of the reaction period 0.4 g of crushed ice was added to the paste with careful stirring. The cherry-red solution was transferred with H$_2$O (0.13 ml) to a flask containing 0.28 g of crushed ice. A solution NaOH (0.53 g, 13 mmol) in H$_2$O (1.4 ml) was added dropwise; the suspension was heated to reflux, allowed to cool to room temperature, and was placed in a refrigerator overnight the precipitate was collected by filtration, washed well with H$_2$O and air-dried to provide 0.15 g (56%) of 5-benzyl-3-formylindole.

The aldehyde 5-benzyl-3-formylindole (0.15 g, 0.6 mmol), nitromethane (0.9 ml) and ammonium acetate (0.05 g, 0.7 mmol) were heated gently under reflux for 0.5 h. On cooling, dark ruby-red crystals slowly separated. Crystallization from methanol gave 0.06 g (34%) of 5-benzyl-3-(2-nitroethenyl)indole as orange crystals.

A solution of the 5-benzyl-3-(2-nitroethenyl)indole (0.1 g, 0.4 mmol)in dry THF was added dropwise to a cooled (ice bath) suspension of LiAlH$_4$ (0.1 g, 2.4 mmol)in 5 ml of dry THF under nitrogen. The mixture was heated at reflux for 45 min. Excess LiAlH$_4$ was destroyed by successive addition of H$_2$O (0.15 ml), 15% NaOH (0.15 ml) and H$_2$O (0.4 ml). The white precipitate was removed by filtration and washed with THF (10 ml). After drying (MgSO$_4$), the flitrate was evaporated under reduced pressure to give 0.04 g (45%) of 3-(2-aminoethyl)-5-benzylindole as a free base. The free base was converted to the fumarate salt, mp 150°–153° C.

EXAMPLE 6

3-(2-aminoethyl)-5-(2-phenylethyl)-indole

A solution of p-nitrostilbene (2 g, 10 mmol) in absolute EtOH (90 ml) and 10% Pd/C (0.250 g) was hydrogenated at room temperature (50 psi) for 24 h. The catalyst was removed by filtration and the solvent was evaporated under reduced pressure until a solid was precipitated. The solid (side product) was separated by filtration and the flitrate was treated with ethereal HCl to provide 0.64 g (31%) of p-(2-phenylethyl)aniline hydrochloride mp 195°–198° C.

Solid NaNO$_2$ (0.35 g, 5 mmol) was added to a suspension of the p-phenethylaniline hydrochloride (1.1 g, 5 mmol) and concentrated HCl (2 ml) in H$_2$O (3 ml) under an icewater bath. The solution was kept at −5° C. with stirring while ethyl 2-methylacetoacetate (0.72 g, 5 mmol)in EtOH 95% (5 ml) was treated at −10° C. with a solution of 50% KOH (1.7 ml) followed at once by ice (10 g). The diazo-solution was then added immediately, stirred at room temperature for 20 min, and extracted with Et$_2$O (2×20 ml). The combined Et$_2$O portions were dried (MgSO$_4$) and the solvent was removed under reduced pressure to give a red oil which was taken up in anhydrous EtOH (10 ml), and dry hydrogen chloride gas was passed through the solution until ammonium chloride was precipitated. The mixture was heated at reflux for 20 min, and then stirred at room temperature for 2 h. The suspension was poured into ice water (100 ml) and extracted with Et$_2$O (2×30 ml). The combined Et$_2$O portions were dried (MgSO$_4$) and the solvent was removed under reduced pressure to give a solid which was recrystallized from EtOH 95% to provide 3-ethyloxycarbonyl-5-(2-phenylethyl)indole.

To a solution of the 3-ethyloxycarbonyl-5-phenethylindole (0.4 g, 1.5 mmol) in EtOH 95% (10 ml) was added an excess of KOH (0.5 g) and the reaction mixture was heated at reflux for 2 h. The solution was acidified with 1N HCl (10 ml) and the precipitated material was collected by filtration. The solid was washed well with H$_2$O (2×10 ml) to give the corresponding acid. The acid (0.3 g, 1.2 mmol) was immersed in an oil bath and then heated at about 235°–240° C. for 15 min to give a brown syrup. Distillation of the oil under high vacuum provided 5-phenethylindole.

Freshly distilled POCl$_3$ (0.122 ml) was added dropwise to cooled (ice bath) dry DMF (0.4 ml). The mixture was stirred 0.5 h at 0° C., then a solution of the 5-phenylindole (0.24 g, 1.2 mmol) in DMF (0.14 ml) was added dropwise, during which time the temperature was maintained below 10° C. Once the solution was well mixed, the temperature was brought to 35° C. The syrup was stirred efficiently at this temperature for 1 h. At the end of the reaction period 0.4 g of crushed ice was added to the paste with careful stirring. The solution was transferred with H$_2$O (0.13 ml) to a flask containing 0.28 g of crushed ice. A solution NaOH (0.53 g, 13 mmol) in H$_2$O (1.4 ml) was added dropwise; the suspension was heated to reflux, allowed to cool to room temperature, and was placed in a refrigerator overnight the precipitate was collected by filtration, washed well with H$_2$O and air-dried to provide 5-(2-phenylethyl)-3-formylindole.

The aldehyde 5-phenethyl-3-formylindole (0.15 g, 0.6 mmol), nitromethane (0.9 ml) and ammonium acetate (0.05 g, 0.7 mmol) were heated gently under reflux for 0.5 h. On cooling, crystals slowly separated. Crystallization from methanol gave of 5-( 2-phenylethyl)-3-(2-nitroethenyl)indole as crystals.

A solution of the 5-phenethyl-3-(2-nitroethenyl)indole (0.1 g, 0.4 mmol)in dry THF was added dropwise to a cooled (ice bath) suspension of LiAlH$_4$ (0.1 g, 2.4 mmol) in 5 ml of dry THF under nitrogen. The mixture was heated at reflux for 45 min. Excess LiAlH$_4$ was destroyed by successive addition of H$_2$O (0.15 ml), 15% NaOH (0.15 ml) and H$_2$O (0.4 ml). The precipitate was removed by filtration and washed with THF (10 ml). After drying (MgSO$_4$), the filtrate was evaporated under reduced pressure to give (56% yield) 3-(2-aminoethyl)-5-(2-phenylethyl)indole, a beige solid; mp 234°–236° C.

EXAMPLE 7

3-(2-aminoethyl)-5-(2-(4-methoxyphenyl)ethyl)indole

A suspension of p-nitrophenylacetic acid (9.05 g, 50 mmol), 4-methoxybenzaldehyde (7.5 g, 55.1 mmol), and piperidine (2.5 ml) was heated at reflux for 45 min. After allowing to cool to room temperature, the reaction mixture was dissolved in CH$_2$Cl$_2$ (100 ml), washed with 0.1N NaOH (2×20 ml), and dried (MgSO$_4$). The solvent was removed under reduced pressure to provide a solid which was recrystallized from EtOH to give 5.8 g (45.5%) of 4-methoxy-4-nitrostilbene as orange-colored crystals, mp 131°–132° C.

A suspension of the 4-methoxy-4'-nitrostilbene 9.4 g, 25 mmol) in 95% EtOH (120 ml) was treated with Raney nickel (7 g, washed with EtOH) in a Parr hydrogenation bottle and then hydrogenated at 50 psi for 20 h. The catalyst was removed by filtration through a Celite pad. The flitrate was concentrated under reduced pressure to give a solid which was recrystallized from hexane to give 4.1 g (72% ) of p-(2-(4-methoxy-2phenyl)ethyl)aniline, mp 98°–99° C. The free base was treated with anhydrous HCl gas to give a solid which was recrystallized from 95% EtOH to give 4.3 g (91%) of the HCl salt as a white solid, mp 234°–235° C. with decomposition.

Solid NaNO$_2$ (1.17 g, 17 mmol) was added to a suspension of p-(2-(4-methoxy- 2phenyl)ethyl)aniline (3 g, 11.4 mmol,) and concentrated HCl (6 ml)in water (35 ml) under an ice-water bath. The solution was kept at 0° C. with stirring while ethyl 20 methylacetoacetate (2.45 g, 17 mmol) in 95% EtOH (15 ml) was treated at 0° C. with a solution of 50% KOH (12 ml) followed at once by ice (20 g). The diazo-solution was then added immediately, stirred at room temperature for 1 h and extracted with Et$_2$O (2×40 ml). The combined Et$_2$O portions were washed with water (1×50 ml), dried (MgSO$_4$), and the solvent was removed under reduced pressure to give a red oil which was taken up in anhydrous EtOH (11 ml) at 0° C. Anhydrous EtOH (30 ml) saturated at 0° C. with anhydrous HCl gas was added to the stirred solution, heated at reflux for 30 min, and then stirred at room temperature for 2 h. The suspension was poured into cold water (200 ml) and extracted with Et$_2$O (2×100 ml) the combined Et$_2$O portions were washed with water (2×150 ml), dried (MgSO$_4$), and the solvent was removed under reduced pressure to give a solid which was recrystallized from CH$_2$Cl$_2$/hexane to provide 1.48 g (41.6%) of 3-ethyloxycarbonyl-5-(2-(4-methoxy-2-phenyl)ethyl)indole as a yellow solid, mp 139°–140° C.

A solution of KOH (0.61 g) in water (2 ml) was added to a suspension of 3-ethyloxycarbonyl-5-(2-(4-methoxy-2-phenyl)ethyl)indole (0.47 g, 1.45 mmol) and heated at reflux for 1 h to give a clear solution. The solution was acidified with glacial acetic acid and the precipitated materials were collected by filtration. The solid was washed well with water (2×10 ml) to give 0.42 g (98%) of the corresponding acid as an ivory-colored solid, mp 194°–195° C. A mixture of the acid (0.5 g, 1.69 mmol), freshly distilled quinoline (5 ml), and copper chromite (0.1 g) was immersed in an oil bath and then heated at about 240° C. for 3 h under nitrogen. The cooled brown syrup was poured into Et$_2$O (50 ml); the solution was stirred with activated carbon (Darco G-60, 100 mesh), filtered, and washed successively with 2NHCl (4×20 ml) and 2N NaOH (2×20 ml). The solution was washed with water (3×20 ml), stirred with activated carbon, filtered, and dried (MgSO$_4$). The solvent was removed under reduced pressure to give a light-yellow oil that solidified on standing at room temperature. The solid was recrystallized from EtoAc/hexane to give 0.25 g (59%) of 5-(2-(4-methoxy-2-phenyl)ethyl)indole as white crystals mp 77°–78° C.

A solution of oxalyl chloride (0.35 g, 2.77 mmol) in anhydrous Et$_2$O (5 ml) was added over 5 min period to a solution of the 5-(2-(4-methoxy-2-phenyl)ethyl)indole (0.58 g, 2.31 mmol) in anhydrous Et$_2$O (10 ml) at 0° C. The reaction mixture was allowed to stir at room temperature for 1 h. The bright yellow precipitate that formed was collected by filtration, washed with anhydrous $Et_2O$ (2×20 ml), and immediately added to concentrated $NH_4OH$ (10 ml) at 0° C. The basic solution was allowed to stir at room temperature overnight and the solid was collected by filtration, washed with water (2×20 ml), air-dried, and recrystallized from acetone/hexane to afford 0.62 g (83%) of the amide as a light yellow solid; mp 224°–225° C.

A suspension of the amide (1 g, 3.1 mmol) and $LiAlH_4$ was decomposed by the addition of a saturated solution of sodium potassium tartrate (5 ml) at 0° C. The precipitated material was removed by filtration and the flitrate was dried ($MgSO_4$). The solvent was removed under reduced pressure to afford an oily product. The resulting oil was purified by column chromatography using a solvent system of $CH_2Cl_2$/MeOH (90:10). The combined fractions from the column were evaporated under reduced pressure to give a solid. Without further purification, a solution of this free base in MeOH (5 ml) was treated with a solution of oxalic acid dihydrate in MeOH (5 ml). The solvent was removed under reduced pressure to afford an oil which was crystallized from MeOH/$Et_2O$ to give 0.32 g (26%) of 3-(2-aminoethyl)-5-(2-(4-methoxyphenyl)ethyl)indole as light-yellow flakes, mp 165°–167° C.

EXAMPLE 8

Comparison of Binding Affinities

Compounds of the previous examples 1–7, as well as reference compounds, were evaluated for binding affinity using cell types receptive specifically to 5-HT1Dβ ligands. The assay protocol generally entailed the incubation of membranes prepared from cells expressing the 1Dβ sub-type of 5-HT1D receptors, with $^3$H-5-HT. Increasing concentrations of the test compound were incubated with the radioligand and the membrane homogenates prepared from the recombinant cells. After a 15 minute incubation at 37° C., the incubation was terminated by vacuum filtration. The filters were washed with buffer and counted for radioactivity using liquid scintillation spectrometry. The affinity of the test compound for 5-HT1DIβ receptor was determined by computer-assisted analysis of the data and by determining the amount of the compound necessary to inhibit 50% of the binding of the radioligand. Concentrations ranging from $10^{-11}$M to $10^{-5}$M of the test compounds were evaluated. For comparison, sumatriptan, and other compounds structurally related to the test compounds were also evaluated. The results are presented in Table 1 below, with reference to the Formula (I) in which $R^2$ and $R^3$ are both hydrogen.

TABLE 1

| $R^1$ | Compound | 5-HT1Dβ (Ki, nM) |
|---|---|---|
| 5-HT | serotonin | 4.0 |
| $CH_2NH-SO_2-CH_2-$ | sumatriptan | 5.5 |
| $PhCH_2O-$ | reference | 10.5 |
| $Ph(CH_2)_2O-$ | example | 1.0 |
| $Ph(CH_2)_4O-$ | example | 0.19 |
| $Ph(CH_2)_5O-$ | example | 0.64 |
| $Ph(CH_2)_6O-$ | example | 1.9 |
| $PhCH_2-$ | example | 3.7 |
| $Ph(CH_2)_2-$ | example | 2.9 |
| $4-MeO-Ph(CH_2)_2-$ | example | 3.2 |
| $Ph(CH_2)_8O-$ | reference | 13.3 |

When $R^1$ is selected from the aryl-alkoxy it can be seen that binding affinity for 5-HT1D receptors is dramatically enhanced when the alkyl chain portion of the group is extended beyond one carbon atom. Also, the tabulated results reveal that binding affinity is preserved when the aryl group is substituted.

We claim:

1. A compound of the formula:

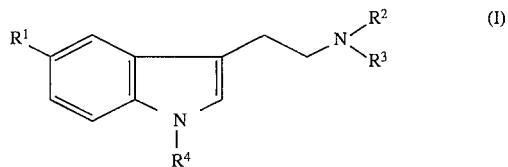

wherein $R^1$ is a group selected from aryl-$C_{1-7}$alkyl; aryl-$C_{2-7}$alkoxy; aryl-$C_{2-7}$alkanoyl and aryl-$C_{3-7}$alkanoyloxy, wherein said alkyl, alkoxy, alkanoyl and alkanoyloxy groups are optionally substituted by a $C_{1-4}$alkyl substituent and wherein said aryl group is optionally substituted by one or more substituents selected from hydroxyl, halogen, mercapto, linear or branched $C_{1-4}$alkyl, linear or branched $C_{1-4}$alkoxy, linear or branched $C_{1-4}$alkylthio, thiol substituted $C_{1-4}$alkyl and nitro substituted $C_{1-4}$alkyl;

$R^2$ and $R^3$ are selected independently from H and $C_{1-4}$alkyl; and $R^4$ is selected from H, $C_{1-4}$ alkyl, aryl and aryl$C_{1-4}$alkyl.

2. A compound according to claim 1, wherein $R^1$ is aryl-$C_{2-7}$alkoxy.

3. A compound according to claim 2, wherein $R^2$, $R^3$ and $R^4$ are each hydrogen.

4. A compound according to claim 3, wherein $R^1$ is 4-phenylbutyloxy.

5. A compound according to claim 3, wherein $R^1$ is 5-phenylpentyloxy.

6. A compound according to claim 3, wherein $R^1$ is 6-phenylhexyloxy.

7. A compound according to claim 3, wherein $R^1$ is 2-phenylethyloxy.

8. A compound according to claim 1, wherein $R^1$ is aryl-$C_{1-7}$alkyl.

9. A compound according to claim 8, wherein $R^2$, $R^3$ and $R^4$ are each hydrogen.

10. A compound according to claim 9, wherein $R^1$ is benzyl.

11. A compound according to claim 9, wherein $R^1$ is 2-phenylethyl

12. A compound according to claim 9, wherein $R^1$ is 2-(p-methoxyphenyl)ethyl.

13. A compound according to claim 1, wherein $R^1$ is aryl-$C_{2-7}$alkanoyl and $R^2$, $R^3$ and $R^4$ are each hydrogen.

14. A compound according to claim 1, wherein $R^1$ is aryl-$C_{3-7}$alkanoyloxy and $R^2$, $R^3$ and $R^4$ are each hydrogen.

15. A compound according to claim 1, in radiolabelled form.

16. A compound according to claim 4, in radiolabelled form.

17. A pharmaceutical composition, comprising a pharmaceutically acceptable carrier and a compound as defined in claim 1.

18. A pharmaceutical composition, comprising a pharmaceutically acceptable carrier and a compound as defined in claim 4.

19. A pharmaceutical composition, comprising a pharmaceutically acceptable carrier and a compound as defined in claim 5.

20. A pharmaceutical composition, comprising a pharmaceutically acceptable carrier and a compound as defined in claim 6.

\* \* \* \* \*